(12) United States Patent
Aoyagi (10) Patent No.: US 10,552,694 B2
(45) Date of Patent: Feb. 4, 2020

(54) DROWSINESS ESTIMATING APPARATUS (71) Applicant: TOYOTA JIDOSHA KABUSHIKI KAISHA, Toyota-shi, Aichi-ken (JP)

(72) Inventor: Isao Aoyagi, Nagakute (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/177,683

(22) Filed: Nov. 1, 2018

(65) Prior Publication Data
US 2019/0197329 A1 Jun. 27, 2019

(30) Foreign Application Priority Data

Dec. 22, 2017 (JP) .................................. 2017-246603

(51) Int. Cl.
*G06K 9/00* (2006.01)
*A61B 5/18* (2006.01)
*A61B 5/11* (2006.01)
*B60H 1/00* (2006.01)
*B60Q 9/00* (2006.01)

(52) U.S. Cl.
CPC ........ *G06K 9/00845* (2013.01); *A61B 5/1128* (2013.01); *A61B 5/18* (2013.01); *B60H 1/00742* (2013.01); *G06K 9/00302* (2013.01); *B60H 1/00964* (2013.01); *B60Q 9/00* (2013.01)

(58) Field of Classification Search
None
See application file for complete search history.

(56) References Cited

U.S. PATENT DOCUMENTS

| 6,927,694 | B1 * | 8/2005 | Smith | B60K 28/066 340/573.1 |
| 2009/0268022 | A1 * | 10/2009 | Omi | A61B 5/18 348/135 |
| 2010/0007665 | A1 * | 1/2010 | Smith | G06T 13/40 345/473 |
| 2010/0214087 | A1 * | 8/2010 | Nakagoshi | A61B 5/18 340/436 |
| 2010/0265074 | A1 * | 10/2010 | Namba | G06K 9/00771 340/576 |
| 2011/0235919 | A1 * | 9/2011 | Morita | A61B 5/18 382/195 |
| 2013/0021463 | A1 | 1/2013 | Hatakeyama | |

(Continued)

FOREIGN PATENT DOCUMENTS

| JP | 2008-212298 A | 9/2008 |
| JP | 2009-045418 A | 3/2009 |

(Continued)

*Primary Examiner* — Chico A Foxx
(74) *Attorney, Agent, or Firm* — Oliff PLC (57) ABSTRACT

A drowsiness estimating apparatus is provided with: an imager configured to take a face image of a driver of a vehicle; a detector configured to detect a duration of a mouth movement of the driver and whether or not the mouth movement has periodicity, on the basis of the face image; a determinator configured to determine a type of the mouth movement on the basis of the duration and whether or not the mouth movement has the periodicity; and an estimator configured to estimate drowsiness of the driver on the basis of the type of the mouth movement.

4 Claims, 12 Drawing Sheets

(56) References Cited

U.S. PATENT DOCUMENTS

| | | | | |
|---|---|---|---|---|
| 2013/0194099 A1* | 8/2013 | Nagata | ............... | B60K 28/06 |
| | | | | 340/575 |
| 2014/0313333 A1* | 10/2014 | Le | ............... | B60R 16/0231 |
| | | | | 348/148 |
| 2015/0363657 A1* | 12/2015 | Shigemura | ............... | A61B 5/18 |
| | | | | 382/104 |
| 2016/0046298 A1* | 2/2016 | DeRuyck | ............... | B60W 40/09 |
| | | | | 340/576 |
| 2016/0262682 A1* | 9/2016 | Omi | ............... | A61B 5/18 |
| 2016/0272217 A1* | 9/2016 | Kim | ............... | B60K 28/066 |
| 2018/0012090 A1* | 1/2018 | Herbst | ............... | G06K 9/00845 |
| 2018/0319279 A1* | 11/2018 | Ikeda | ............... | G01C 21/3484 |
| 2018/0330177 A1* | 11/2018 | Ryu | ............... | G06K 9/00845 |
| 2019/0026544 A1* | 1/2019 | Hua | ............... | G06T 7/194 |
| 2019/0065873 A1* | 2/2019 | Wang | ............... | G06K 9/00845 |
| 2019/0162549 A1* | 5/2019 | Fouad | ............... | G01C 21/3484 |

FOREIGN PATENT DOCUMENTS

| | | | | |
|---|---|---|---|---|
| JP | 5228970 B2 | | 7/2013 | |
| JP | 2013156707 | * | 8/2013 | ............... B60R 1/00 |
| JP | 5447657 B2 | | 3/2014 | |

* cited by examiner

| Mouth movement type | Drowsiness |
|---|---|
| None | Not drowsy |
| Mouth movement by drowsiness | Drowsy |
| Eating | Not drowsy |
| Conversation | Not drowsy |

FIG. 7

| Mouth movement type | Drowsiness |
|---|---|
| None | Not drowsy |
| Mouth movement by drowsiness | Drowsy |
| Eating (For a long time) | Drowsy |
| Eating (For a short time) | Not drowsy |
| Conversation | Not drowsy |

|  |  | Drowsiness determination by eyes | | | |
|---|---|---|---|---|---|
|  |  | Not drowsy | Slightly drowsy | Drowsy | Very drowsy |
| Mouth movement type | None | Not drowsy | Slightly drowsy | Drowsy | Very drowsy |
|  | Mouth movement by drowsiness | Slightly drowsy | Drowsy | Very drowsy | Very drowsy |
|  | Eating | Not drowsy | Slightly drowsy | Drowsy | Very drowsy |
|  | Conversation | Not drowsy | Slightly drowsy | Drowsy | Very drowsy |

FIG. 12

|  |  | Drowsiness determination by eyes | | | |
|---|---|---|---|---|---|
|  |  | Not drowsy | Slightly drowsy | Drowsy | Very drowsy |
| Mouth movement type | None | Not drowsy | Slightly drowsy | Drowsy | Very drowsy |
| | Mouth movement by drowsiness | Slightly drowsy | Drowsy | Very drowsy | Very drowsy |
| | Eating (Long time) | Slightly drowsy | Drowsy | Very drowsy | Very drowsy |
| | Eating (Short time) | Not drowsy | Slightly drowsy | Drowsy | Very drowsy |
| | Conversation | Not drowsy | Slightly drowsy | Drowsy | Very drowsy |

DROWSINESS ESTIMATING APPARATUS

CROSS-REFERENCE TO RELATED APPLICATIONS

This application is based upon and claims the benefit of priority of the prior Japanese Patent Application No. 2017-246603, filed on Dec. 22, 2017, the entire contents of which are incorporated herein by reference.

BACKGROUND

1. Technical Field

Embodiments of the present disclosure relate to a drowsiness estimating apparatus configured to estimate drowsiness or sleepiness of an occupant of a vehicle.

2. Description of the Related Art

For this type of imaging apparatus, there is known an apparatus configured to estimate the drowsiness or sleepiness (in other words, an awakening degree) from the movement of the occupant of the vehicle. For example, Japanese Patent Application Laid Open No. 2008-212298 (Patent Literature 1) discloses a technology/technique in which face images of a driver are taken and the drowsiness of the driver is determined on the basis of at least one of eye movement (e.g., a time in a half-open eye state, an eye closing time, an eye opening time, etc.) and mouth movement (e.g., partly opening the mouth, pursing up lips, etc.). Japanese Patent Application Laid Open No. 2009-045418 (Patent Literature 2) discloses a technology/technique in which a drowsiness degree is determined on the basis of two or more facial expression information obtained (including, for example, a distance between left and right corners of a mouth, a distance between a middle point of inner corners of eyebrows and a middle point of inner corners of eyes, a distance between an upper eyelid and a lower eyelid, etc.). Japanese Patent No. 05447657 (Patent Literature 3) discloses a technology/technique in which an absentminded state before feeling drowsy is detected from a variation in the eye opening time and a variation in a face direction.

In addition, as a measure when the drowsiness is detected, there is known an apparatus configured to give an awakening stimulus to the occupant of the vehicle. For example, Japanese Patent No. 05228970 (Patent Literature 4) discloses a technology/technique in which the intensity of a provided awakening stimulus is adjusted in accordance with the degree of the drowsiness detected.

In the aforementioned Patent Literature 1, the drowsiness is determined by using the mouth movement; however, there are various types of mouth movements (e.g., a movement by conversation, a movement by eating, a movement by drowsiness, etc.) and there is a possibility that the drowsiness cannot be accurately determined only from a simple movement.

In other words, the drowsiness cannot be accurately estimated without determining what actually causes the mouth movement, which is technically problematic.

SUMMARY

In view of the aforementioned problems, it is therefore an object of embodiments of the present disclosure to provide a drowsiness estimating apparatus configured to accurately estimate the drowsiness by using the mouth movement.

The above object of embodiments of the present disclosure can be achieved by a drowsiness estimating apparatus is provided with: an imager configured to take a face image of a driver of a vehicle; a detector configured to detect a duration of a mouth movement of the driver and whether or not the mouth movement has periodicity, on the basis of the face image; a determinator configured to determine a type of the mouth movement on the basis of the duration and whether or not the mouth movement has the periodicity; and an estimator configured to estimate drowsiness of the driver on the basis of the type of the mouth movement.

DETAILED DESCRIPTION OF THE EMBODIMENTS

Hereinafter, a drowsiness estimating apparatus according to embodiments will be explained with reference to the drawings.

First Embodiment

A drowsiness estimating apparatus according to a first embodiment will be explained with reference to FIG. 1 to FIG. 8.

<Configuration of Apparatus>

Figure 1:
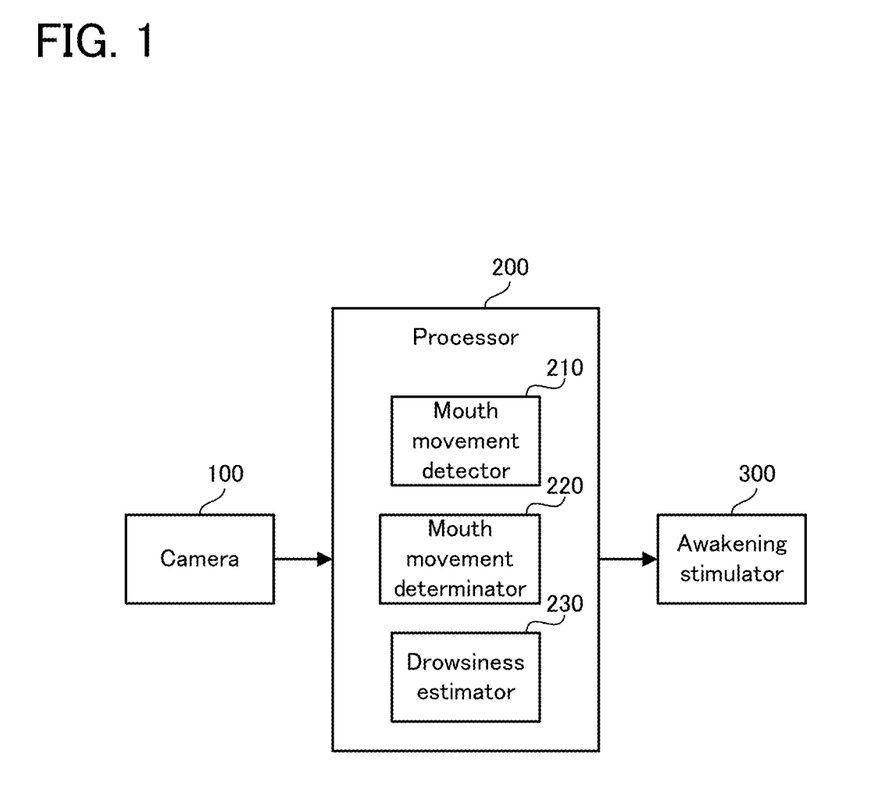
FIG. 1 is a block diagram illustrating a configuration of a drowsiness estimating apparatus according to a first embodiment.

Firstly, a configuration of the drowsiness estimating apparatus according to the first embodiment will be explained with reference to FIG. 1. FIG. 1 is a block diagram illustrating the configuration of the drowsiness estimating apparatus according to the first embodiment.

As illustrated in FIG. 1, the drowsiness estimating apparatus according to the first embodiment is provided with a camera 100, a processor 200, and an awakening stimulator 300.

The camera 100 is, for example, an in-vehicle camera, and may be located at a position at which a face (which is specifically near eyes and a mouth) of a driver of a vehicle can be imaged. Image data taken or captured by the camera 100 may be outputted to the processor 200. The camera 100 is a specific example of the "imager" in Supplementary Notes described later.

The processor 200 is configured to be a controller unit, such as, for example, an electronic control unit (ECU). The processor 200 is provided with a mouth movement detector 210, a mouth movement determinator 220, and a drowsiness estimator 230. The mouth movement detector 210 is a specific example of the "detector" in Supplementary Notes described later. The mouth movement determinator 220 is a specific example of the "determinator" in Supplementary Notes described later. The drowsiness estimator 230 is a specific example of the "estimator" in Supplementary Notes described later. The operation of each part of the processor 200 will be detailed later. The processor 200 is configured to estimate drowsiness or sleepiness of the driver of the vehicle and is configured to output an estimation result to the awakening stimulator 300.

The awakening stimulator 300 is configured to provide an awakening stimulus (i.e., a stimulus that aims at removing the drowsiness) for the driver of the vehicle. The awakening stimulator 300 may provide a plurality of different awakening stimuli in accordance with the estimation result (i.e., the drowsiness of the driver) outputted from the processor 200. An example of the awakening stimulus is to play audio or music, to send an air by using an air-conditioner, or the like. The awakening stimulator 300 is a specific example of the "provider" in Supplementary Notes described later.

<Mouth Movement Type>

Figure 2:
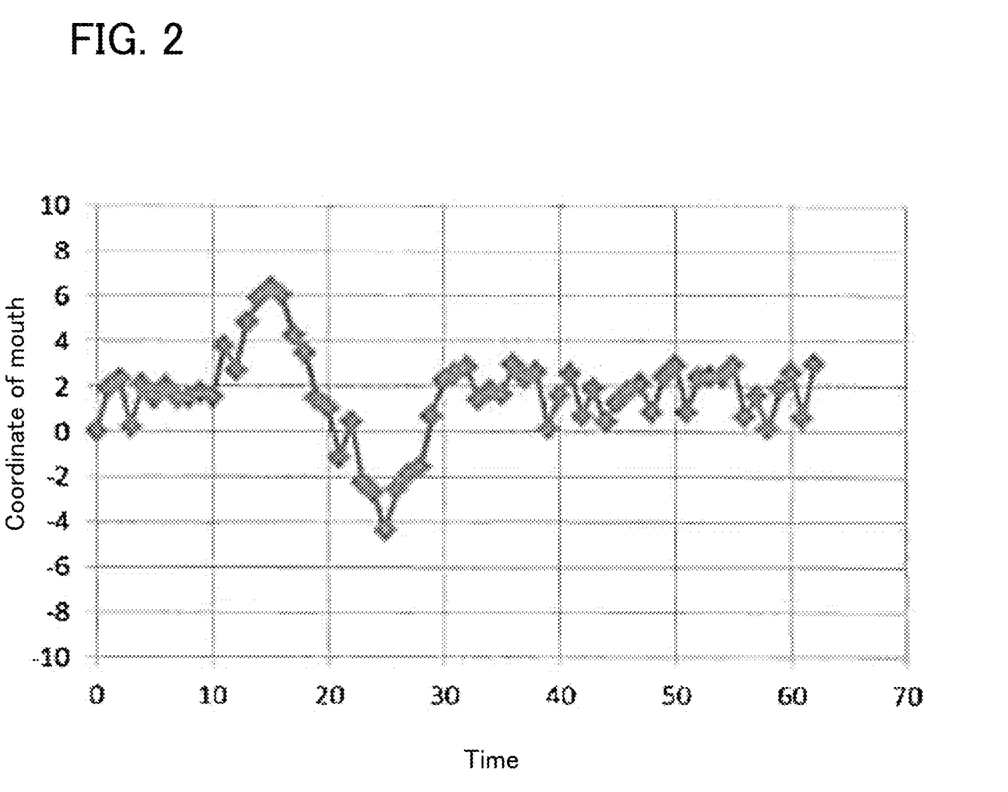
FIG. 2 is a graph illustrating an example of a coordinate change of a mouth movement by drowsiness.
Figure 3:
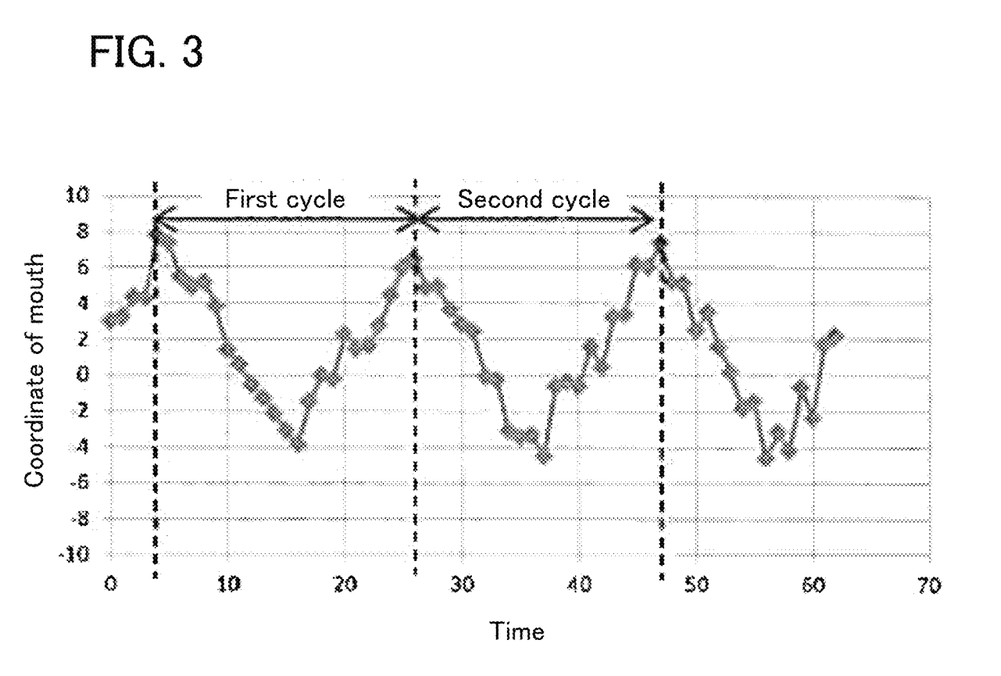
FIG. 3 is a graph illustrating an example of a coordinate change of a mouth movement by eating.
Figure 4:
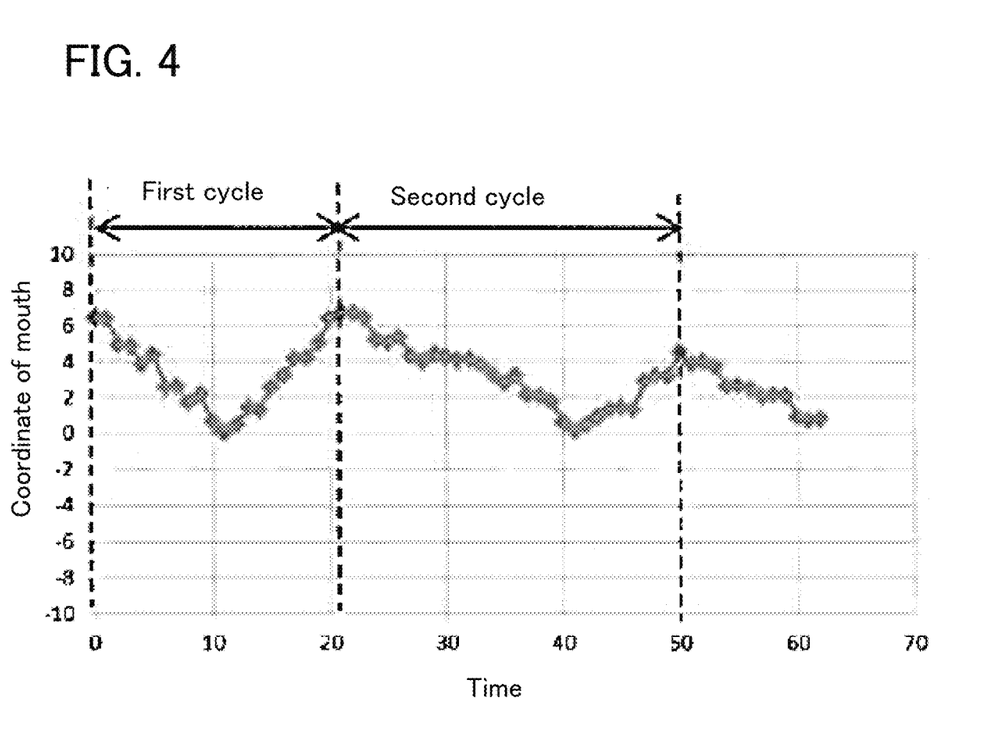
FIG. 4 is a graph illustrating an example of a coordinate change of a mouth movement by conversation.

Next, a "mouth movement type" used when the drowsiness estimating apparatus according to the first embodiment estimates the drowsiness of the driver will be explained with reference to FIG. 2 to FIG. 4. FIG. 2 is a graph illustrating an example of a coordinate change of a mouth movement by drowsiness. FIG. 3 is a graph illustrating an example of a coordinate change of a mouth movement by eating. FIG. 4 is a graph illustrating an example of a coordinate change of a mouth movement by conversation. For each data in FIG. 2 to FIG. 4, one point of the mouth is used as a landmark, and its vertical coordinate (or Y coordinate) is plotted.

As illustrated in FIG. 2 to FIG. 4, the mouth movement has different characteristics depending on what is intended. For example, the mouth movement by drowsiness illustrated in FIG. 2 is temporal, and the movement has no periodicity. Specifically, the coordinate significantly changes in a moment, but does not change for a relatively long time. The mouth movement by eating illustrated in FIG. 3 continues for a relatively long time, and the movement has periodicity. This is because chewing food is a periodic movement. The mouth movement by conversation illustrated in FIG. 4 continues for a relatively long time, but the movement has no periodicity (wherein the first cycle and the second cycle have different time lengths). This is because the mouth does not repeat the same movement in conversation.

The drowsiness estimating apparatus according to the first embodiment is configured to estimate the drowsiness of the driver by classifying the mouth movement of the driver into any of the movement by drowsiness (refer to FIG. 2), the movement by eating (refer to FIG. 3), and the movement by conversation (refer to FIG. 4) described above.

<Mouth Movement Type Determination Operation>

Figure 5:
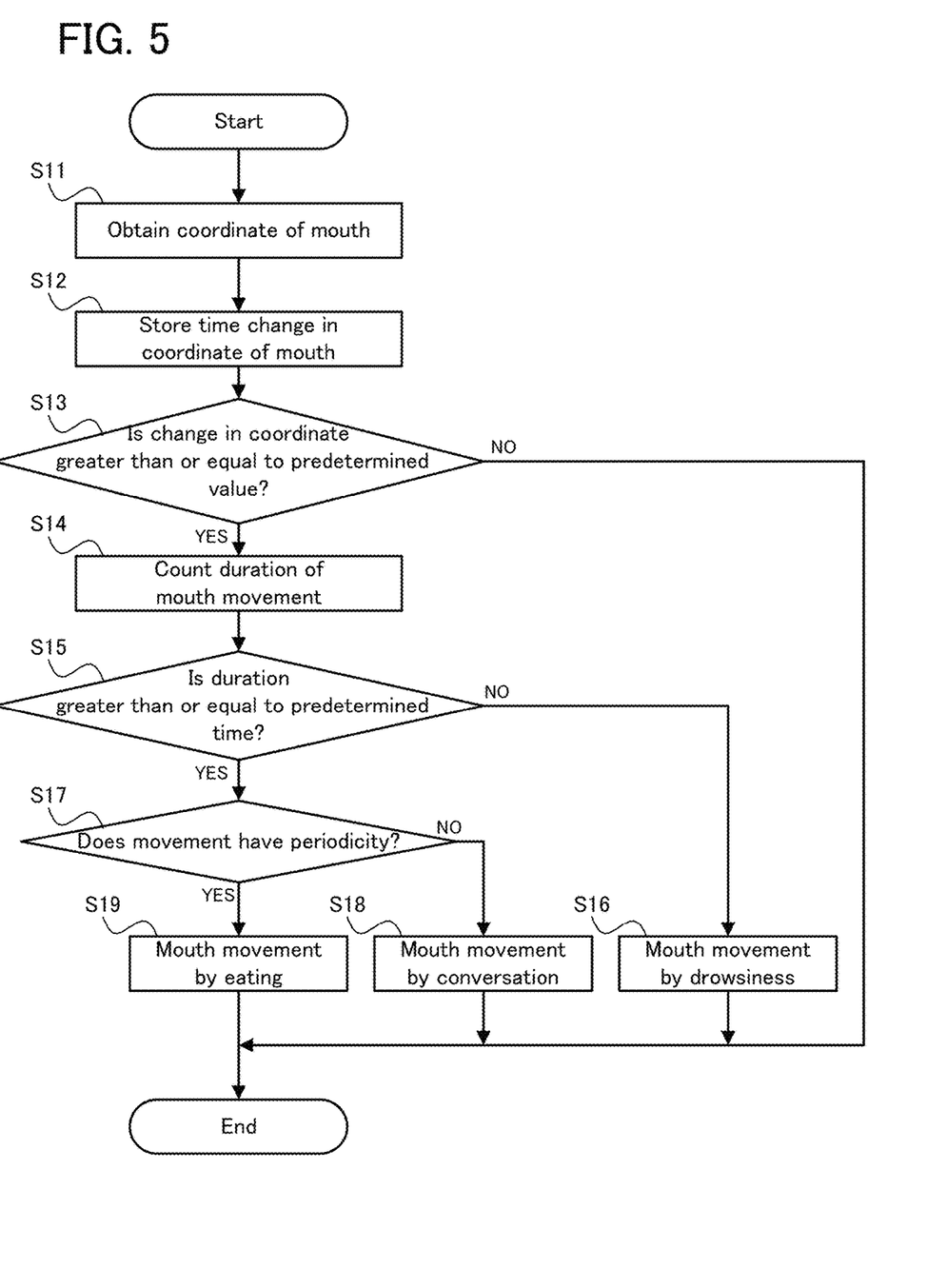
FIG. 5 is a flowchart illustrating a flow of a mouth movement type determination operation performed by the drowsiness estimating apparatus according to the first embodiment.

Next, a mouth movement type determination operation (i.e., an operation of determining the mouth movement type of the driver) performed by the drowsiness estimating apparatus according to the first embodiment will be explained with reference to FIG. 5. FIG. 5 is a flowchart illustrating a flow of the mouth movement type determination operation performed by the drowsiness estimating apparatus according to the first embodiment.

As illustrated in FIG. 5, in the mouth movement type determination operation, firstly, the mouth movement detector 210 obtains the coordinate of the mouth of the driver from the captured images of the camera 100 (step S11). For the coordinate of the mouth, an arbitrary point may be obtained as the landmark, or a plurality of points may be obtained as the landmark. The existing technique/technology can be applied to a specific method of detecting the coordinate, as occasion demands, and a detailed explanation of the method will be omitted here.

Then, the mouth movement detector 210 stores a time change in the coordinate of the mouth (step S12). Specifically, the mouth movement detector 210 may sequentially store a coordinate at t=1, a coordinate at t=2, a coordinate at t=3, . . . , and a coordinate at t=N. The mouth movement detector 210 then determines whether or not the time change in the coordinate is greater than or equal to a predetermined value (step S13). The predetermined value herein may be a value set in advance as a threshold value for determining whether or not there is the mouth movement. The mouth movement detector 210 may determine, for example, whether or not a difference between the coordinate at t=N and a coordinate at t=N+1 is greater than or equal to the predetermined value.

If the time change in the coordinate is not greater than or equal to the predetermined value (the step S13: NO), the mouth movement detector 210 determines that there is no mouth movement, and omits the subsequent process. In this case, the process may be started again from the step S11 after a lapse of a predetermined period. On the other hand, if the time change in the coordinate is greater than or equal to the predetermined value (the step S13: YES), the mouth movement detector 210 determines that there is the mouth movement, and counts a duration of the mouth movement (steps S14). The duration herein may be the number of times in which the coordinate change that is greater than or equal to the predetermined value is continuously detected. The mouth movement detector 210 may increment a count value, for example, every time the change in the coordinate is greater than or equal to the predetermined value.

Then, the mouth movement determinator 220 determines whether or not the duration of the mouth movement is greater than or equal to a predetermined time (step S15). The predetermined time herein may be a threshold value for determining whether or not the mouth movement is the mouth movement by drowsiness, and may be set at an appropriate value, for example, by simulations in advance or the like. If the duration of the mouth movement is not greater than or equal to the predetermined time (the step S15: NO), the mouth movement determinator 220 determines that the mouth movement is the mouth movement by drowsiness (step S16).

On the other hand, if the duration of the mouth movement is greater than or equal to the predetermined time (the step S15: YES), the mouth movement determinator 220 determines whether or not the mouth movement has periodicity (step S17). In determining the presence or absence of the periodicity, for example, if the coordinate at t=0 matches the coordinate at t=N, a period between t=0 and t=N may be set a candidate of one cycle. It is then subsequently determined whether the coordinate at t=1 matches the coordinate at t=N+1, whether the coordinate at t=2 matches a coordinate at t=N+2, whether the coordinate at t=3 matches a coordinate at t=N+3, and so on. It may be determined that the mouth movement has the periodicity when a matching rate in each case is greater than or equal to a predetermined threshold value.

If the mouth movement has no periodicity (the step S17: NO), the mouth movement determinator 220 determines that the mouth movement is the movement by conversation (step S18). On the other hand, if the mouth movement has the periodicity (the step S17: YES), the mouth movement determinator 220 determines that the mouth movement is the movement by eating (step S19).

<Drowsiness Estimation Operation>

Figure 6:
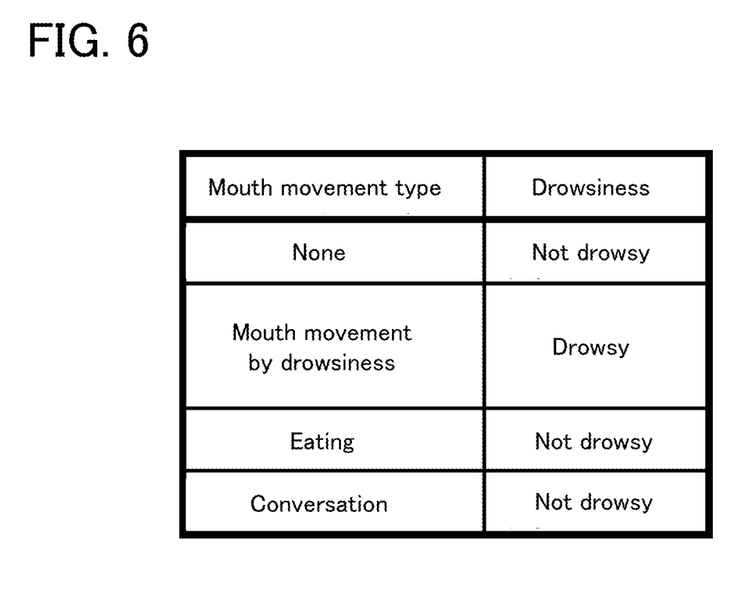
FIG. 6 is version 1 of a lookup table of drowsiness estimation based on a mouth movement type.
Figure 7:
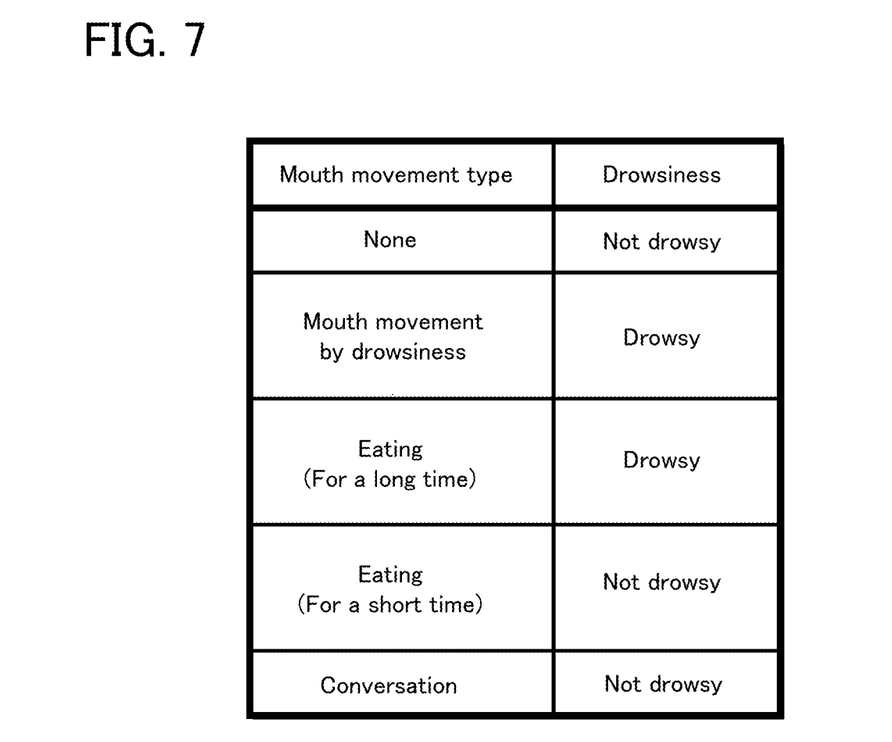
FIG. 7 is version 2 of the lookup table of the drowsiness estimation based on the mouth movement type.

Next, a drowsiness estimation operation (i.e., an operation of estimating the drowsiness of the driver) performed by the drowsiness estimating apparatus according to the first embodiment will be explained with reference to FIG. 6 and FIG. 7. FIG. 6 is version 1 of a lookup table of drowsiness estimation based on the mouth movement type. FIG. 7 is version 2 of the lookup table of the drowsiness estimation based on the mouth movement type.

As illustrated in FIG. 6, the drowsiness estimator 230 is configured to estimate the drowsiness of the driver on the basis of the mouth movement type determined by the mouth movement determinator 220. Specifically, the drowsiness estimator 230 is configured to determine that the driver is not drowsy if there is no mouth movement. The drowsiness estimator 230 is configured to determine that the driver is drowsy if the mouth movement is the movement by drowsiness. The drowsiness estimator 230 is configured to determine that the driver is not drowsy if the mouth movement is the movement by eating. The drowsiness estimator 230 is configured to determine that the driver is not drowsy if the mouth movement is the movement by conversation.

As described above, on the drowsiness estimating apparatus according to the first embodiment, even when the mouth movement is detected, it may be determined that the driver is drowsy if the detected movement is the mouth movement by drowsiness, and it may not be determined that the driver is drowsy if the detected movement is the mouth movement by eating or by conversation. It is therefore possible to more accurately estimate the drowsiness of the driver, in comparison with when the drowsiness is estimated only from the mouth movement.

As illustrated in FIG. 7, regarding the mouth movement by eating, the drowsiness may be estimated in accordance with a length of the duration. Specifically, if the mouth movement by eating continues for a long time, it may be determined that the driver is intentionally eating (e.g., chewing gum) to remove the drowsiness, and it may be estimated that the driver is drowsy. On the other hand, the mouth movement by eating continues for a short time, it may be determined that the driver is having a normal meal, and it may be estimated that the driver is not drowsy.

In considering the duration of the mouth movement by eating, for example, a question, such as "Are you having gum or something?" and "Aren't you drowsy?", may be asked to confirm whether or not the eating by the driver is intended to be awake if the mouth movement continues for a long time.

In the aforementioned embodiment, the estimation is performed by selecting between the driver's being drowsy and the driver's being not drowsy; however, the degree of the drowsiness may be more specifically estimated. For example, the drowsiness of the driver may be estimated at a plurality of stages, such as not drowsy, slightly drowsy, drowsy, and very drowsy. Alternatively, the drowsiness of the driver may be digitized.

<Awakening Stimulus Selection Operation>

Figure 8:
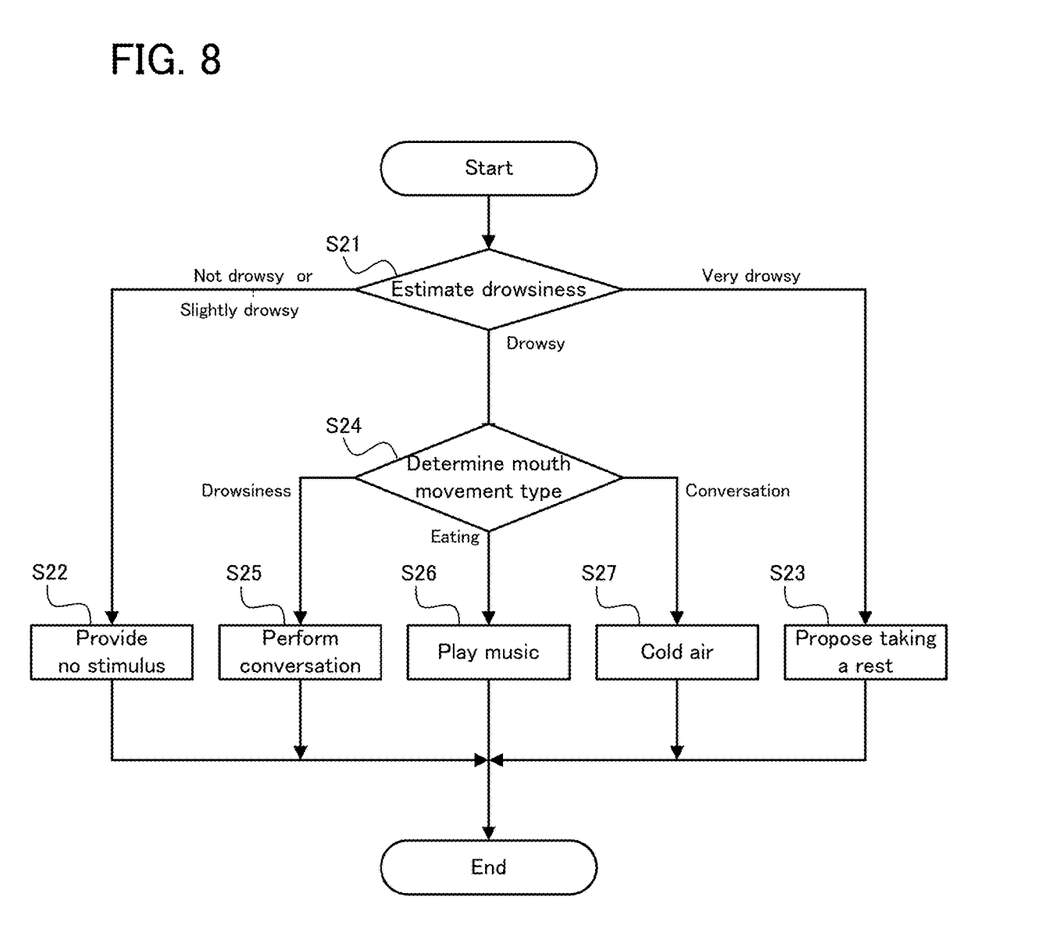
FIG. 8 is a flowchart illustrating a flow of an operation of selecting an awakening stimulus in accordance with the mouth movement type.

Next, an awakening stimulus selection operation (i.e., an operation of selecting the awakening stimulus provided for the driver) performed by the drowsiness estimating apparatus according to the first embodiment will be explained with reference to FIG. 8. FIG. 8 is a flowchart illustrating a flow of the operation of selecting the awakening stimulus in accordance with the mouth movement type.

As illustrated in FIG. 8, as a result of estimating the drowsiness (step S21), if it is estimated that the driver is "not drowsy" or "slightly drowsy", the awakening stimulator 300 does not provide the awakening stimulus (step S22). If it is estimated that the driver is "very drowsy", the awakening stimulator 300 determines that the awakening stimulus alone hardly removes the drowsiness, and proposes taking a rest (i.e., stopping driving) (step S23).

On the other hand, if it is estimated that the driver is "drowsy", the awakening stimulator 300 uses the determination result of the mouth movement type (step S24) to provide different awakening stimuli. Specifically, if the mouth movement is caused by drowsiness, the awakening stimulator 300 performs conversation with the driver who uses a conversation system (step S25). If the mouth movement is caused by eating, the awakening stimulator 300 plays music by using an audio system (step S26). If the mouth movement is caused by conversation, the awakening stimulator 300 controls an air-conditioner to provide a cold air (step S27).

As described above, by providing the different awakening stimuli in accordance with the drowsiness of the driver (in other words, the mouth movement type), it is possible to remove the drowsiness of the driver. For example, if a conversation is provided as the awakening stimulus when the mouth movement is caused by eating, the driver may hardly reply and may feel annoyed. Moreover, if a conversation or playing music is provided as the awakening stimulus when the mouth movement is caused by conversation, the driver's conversation may be interrupted and the driver may feel annoyed. The drowsiness estimating apparatus according to the embodiment, however, is configured to determine the mouth movement type before estimating the drowsiness. It is thus possible to accurately determine a current situation of the driver and to provide an appropriate awakening stimulus. Each of the aforementioned awakening stimuli is an example, and another awakening stimulus may be provided in accordance with the drowsiness of the driver. A plurality of awakening stimuli may be also provided in accordance with the drowsiness of the driver.

Second Embodiment

Next, a drowsiness estimating apparatus according to a second embodiment will be explained with reference to FIG. 9 to FIG. 12. The second embodiment is partially different in configuration and operation from the first embodiment explained above, and the other part is substantially the same. Thus, hereinafter, the different part from those of the first embodiment will be explained in detail, and an explanation of the same part will be omitted, as occasion demands.

<Configuration of Apparatus>

Figure 9:
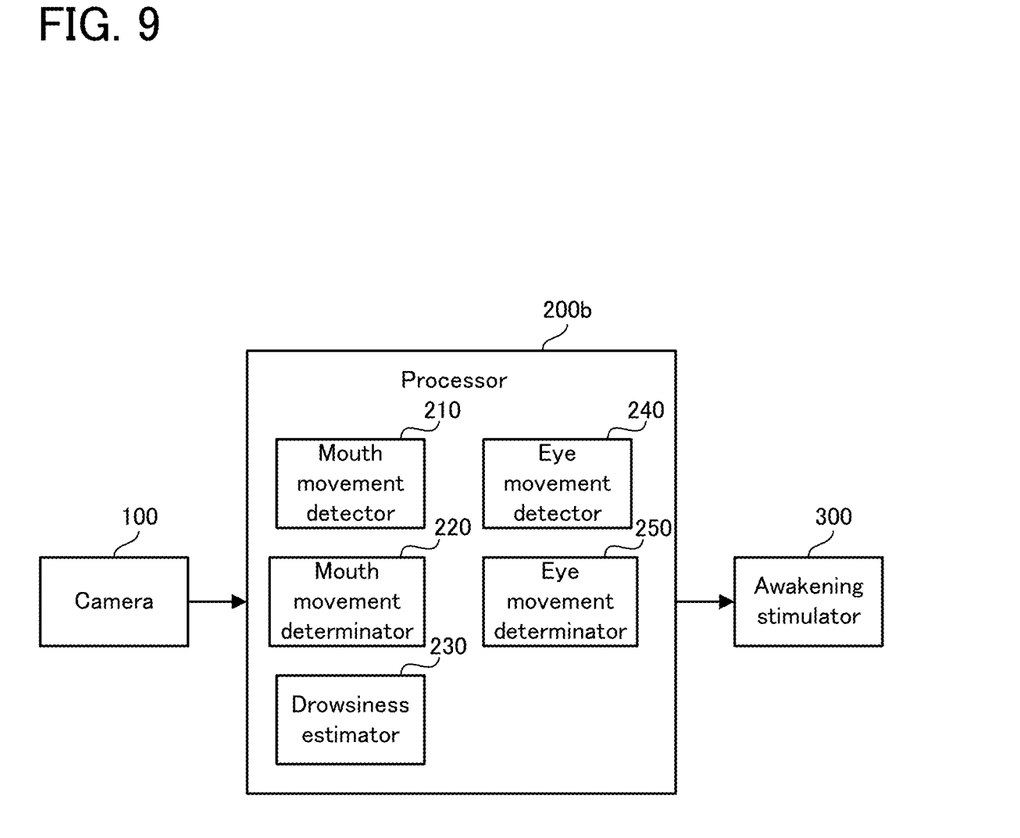
FIG. 9 is a block diagram illustrating a configuration of a drowsiness estimating apparatus according to a second embodiment.

Firstly, a configuration of the drowsiness estimating apparatus according to the second embodiment will be explained with reference to FIG. 9. FIG. 9 is a block diagram illustrating the configuration of the drowsiness estimating apparatus according to the second embodiment.

As illustrated in FIG. 9, a processor 200b according to the drowsiness estimating apparatus according to the second embodiment is provided with an eye movement detector 240 and an eye movement determinator 250, in addition to the configuration in the first embodiment. In other words, the drowsiness estimating apparatus according to the second embodiment is configured to estimate the drowsiness by using an eye movement in addition to the mouth movement.

<Drowsiness Estimation Operation>

Figure 10:
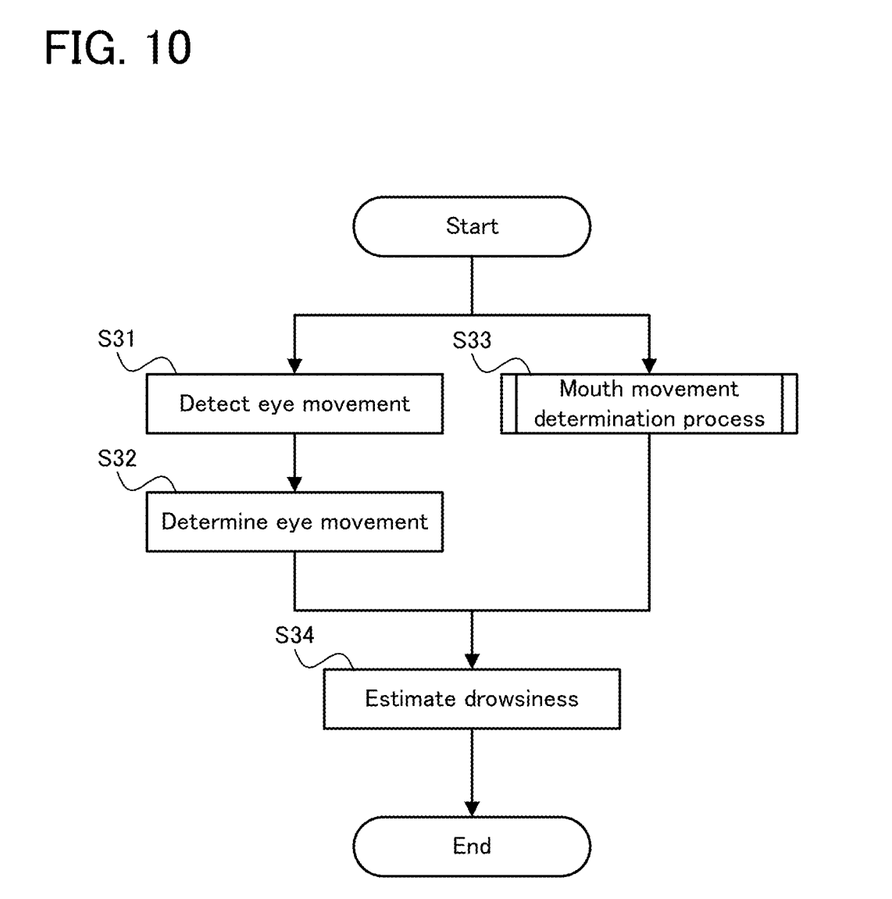
FIG. 10 is a flowchart illustrating a flow of a drowsiness estimation operation performed by the drowsiness estimating apparatus according to the second embodiment.
Figure 11:
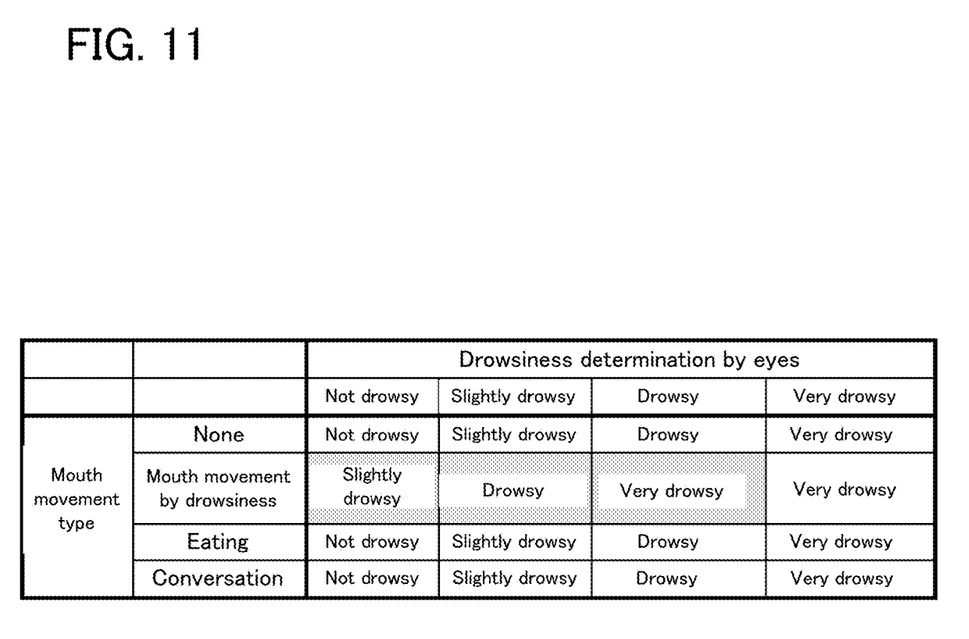
FIG. 11 is version 1 of a lookup table of drowsiness estimation based on an eye movement and the mouth movement.
Figure 12:
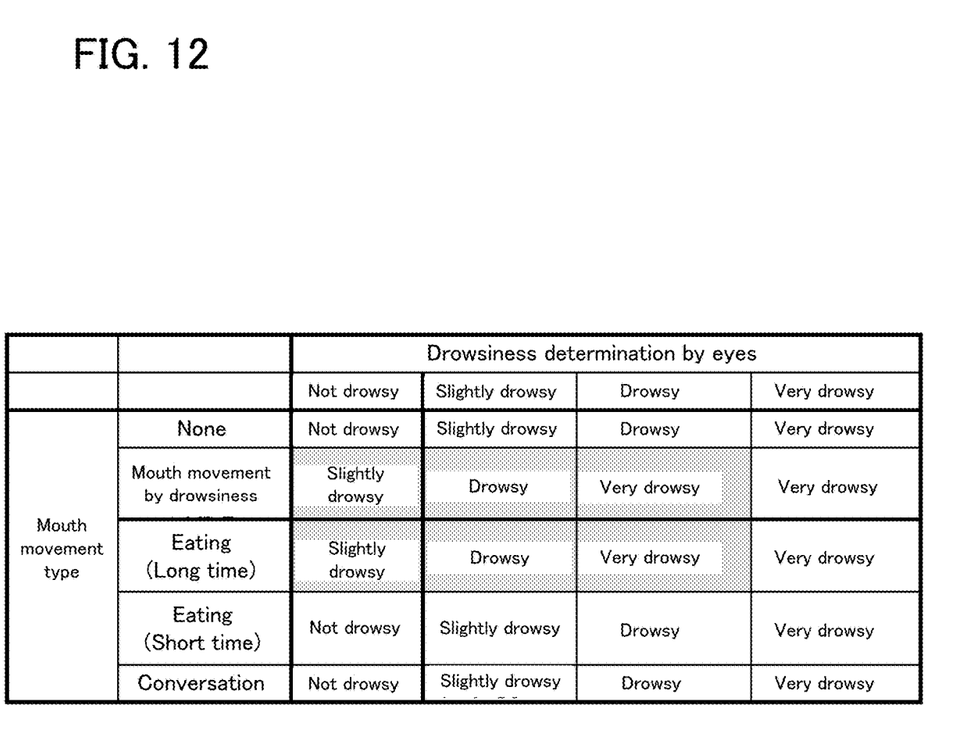
FIG. 12 is version 2 of the lookup table of the drowsiness estimation based on the eye movement and the mouth movement.

Next, a drowsiness estimation operation performed by the drowsiness estimating apparatus according to the second embodiment will be explained with reference to FIG. 10 to FIG. 12. FIG. 10 is a flowchart illustrating a flow of the drowsiness estimation operation performed by the drowsiness estimating apparatus according to the second embodiment. FIG. 11 is version 1 of a lookup table of drowsiness estimation based on the eye movement and the mouth movement. FIG. 12 is version 2 of the lookup table of the drowsiness estimation based on the eye movement and the mouth movement.

As illustrated in FIG. 10, in operation of the drowsiness estimating apparatus according to the second embodiment, the eye movement detector 240 detects the eye movement of the driver (e.g., blinking, moving a line of sight, etc.) from the captured images of the camera 100 (step S31). The existing technique/technology can be applied to a specific method of detecting the eye movement, as occasion demands, and a detailed explanation of the method will be omitted here.

Then, the eye movement determinator 250 provisionally determines the drowsiness of the driver from the detected eye movement (step S32). Specifically, the eye movement determinator 250 may determine the drowsiness of the driver from a blinking speed, a blinking frequency, a line-of-sight moving speed, a line-of-sight moving frequency, or the like. The existing technique/technology can be applied to a method of determining the drowsiness on the basis of the eye movement, as occasion demands, and a detailed explanation of the method will be omitted here.

In parallel with or before or after the step 31 and the step S32 described above, the mouth movement detector 210 and the mouth movement determinator 220 perform a mouth movement determination process (step S33). In other words, as illustrated in the flowchart in FIG. 5, the presence or absence of the mouth movement and the mouth movement type are determined. Then, the drowsiness estimator 230 estimates the drowsiness of the driver on the basis of a determination result of the eye movement and the determination result of the mouth movement (step S34).

As illustrated in FIG. 11, the drowsiness estimator 230 is configured to estimate final drowsiness on the basis of a drowsiness determination result based on the eye movement (hereinafter referred to as "drowsiness determination by eyes", as occasion demands), and the mouth movement type. Specifically, the drowsiness estimator 230 may estimate that the driver is "not drowsy" when the drowsiness determination by eyes provides "not drowsy" "not drowsy" and the mouth movement type is "none". The drowsiness estimator 230 may estimate that the driver is "slightly drowsy" when the drowsiness determination by eyes provides "slightly drowsy" and the mouth movement type is "none". The drowsiness estimator 230 may estimate that the driver is "drowsy" when the drowsiness determination by eyes provides "drowsy" and the mouth movement type is "none". The drowsiness estimator 230 may estimate that the driver is "very drowsy" when the drowsiness determination by eyes provides "very drowsy" and the mouth movement type is "none". The drowsiness estimator 230 may estimate that the driver is "slightly drowsy" when the drowsiness determination by eyes provides "not drowsy" and the mouth movement type is the "movement by drowsiness". The drowsiness estimator 230 may estimate that the driver is "drowsy" when the drowsiness determination by eyes provides "slightly drowsy" and the mouth movement type is the "movement by drowsiness". The drowsiness estimator 230 may estimate that the driver is "very drowsy" when the drowsiness determination by eyes provides "drowsy" and the mouth movement type is the "movement by drowsiness". The drowsiness estimator 230 may estimate that the driver is "very drowsy" when the drowsiness determination by eyes provides "very drowsy" and the mouth movement type is the "movement by drowsiness". The drowsiness estimator 230 may estimate that the driver is "not drowsy" when the drowsiness determination by eyes provides "not drowsy" and the mouth movement type is the "movement by eating". The drowsiness estimator 230 may estimate that the driver is "slightly drowsy" when the drowsiness determination by eyes provides "slightly drowsy" and the mouth movement type is the "movement by eating". The drowsiness estimator 230 may estimate that the driver is "drowsy" when the drowsiness determination by eyes provides "drowsy" and the mouth movement type is the "movement by eating". The drowsiness estimator 230 may estimate that the driver is "very drowsy" when the drowsiness determination by eyes provides "very drowsy" and the mouth movement type is the "movement by eating". The drowsiness estimator 230 may estimate that the driver is "not drowsy" when the drowsiness determination by eyes provides "not drowsy" and the mouth movement type is the "movement by conversation". The drowsiness estimator 230 may estimate that the driver is "slightly drowsy" when the drowsiness determination by eyes provides "slightly drowsy" and the mouth movement type is the "movement by conversation". The drowsiness estimator 230 may estimate that the driver is "drowsy" when the drowsiness determination by eyes provides "drowsy" and the mouth movement type is the "movement by conversation". The drowsiness estimator 230 may estimate that the driver is "very drowsy" when the drowsiness determination by eyes provides "very drowsy" and the mouth movement type is the "movement by conversation".

As described above, if the mouth movement type is "none", the "movement by eating", or the "movement by conversation", then, the result of the drowsiness determination by eyes is used without change for the final drowsiness to be estimated. On the other hand, if the mouth movement type is the "movement by drowsiness", a one-stage higher level of drowsiness than the result of the drowsiness determination by eyes is used for the final drowsiness to be estimated. As described above, if the drowsiness is estimated by using both the eye movement and the mouth movement, it is possible to more accurately estimate the drowsiness, in comparison with when the drowsiness is estimated by using only the eye movement, or only the mouth movement.

As illustrated in FIG. 12, regarding the mouth movement by eating, the drowsiness may be estimated in accordance with the length of the duration. Specifically, if the mouth movement by eating continues for a long time, it may be determined that the driver is intentionally eating to remove the drowsiness, and it may be estimated that the driver has a one-stage higher level of drowsiness than the result of the drowsiness determination by eyes. On the other hand, the mouth movement by eating continues for a short time, it may be determined that the driver is having a normal meal, and the result of the drowsiness determination by eyes may be used without change for the final drowsiness to be estimated.

<Supplementary Notes>

Various aspects of embodiments of the present disclosure derived from the embodiment explained above will be explained hereinafter.

(Supplementary Note 1)

A drowsiness estimating apparatus described in Supplementary Note 1 is provided with: an imager configured to take a face image of a driver of a vehicle; a detector configured to detect a duration of a mouth movement of the driver and whether or not the mouth movement has periodicity, on the basis of the face image; a determinator configured to determine a type of the mouth movement on the basis of the duration and whether or not the mouth movement has the periodicity; and an estimator configured to estimate drowsiness of the driver on the basis of the type of the mouth movement.

According to the drowsiness estimating apparatus described in Supplementary Note 1, the type of the mouth movement (in other words, what causes the mouth movement) may be determined to estimate the drowsiness of the driver. It is thus possible to more accurately estimate the drowsiness, in comparison with when the drowsiness is estimated only from the mouth movement.

(Supplementary Note 2)

In the drowsiness estimating apparatus described in Supplementary Note 2, the determinator is configured to determine that the type of the mouth movement is one of a mouth movement by drowsiness, a mouth movement by eating, and a mouth movement by conversation.

According to this aspect, it is determined whether the mouth movement is caused by drowsiness, by eating, or by conversation, by which it is possible to accurately estimate the drowsiness.

(Supplementary Note 3)

In the drowsiness estimating apparatus described in Supplementary Note 3, the determinator is configured (i) to determine that the type of the mouth movement is the mouth movement by drowsiness if the duration is less than a first predetermined time, (ii) to determine that the type of the mouth movement is the mouth movement by eating if the duration is greater than the first predetermined time and if the mouth movement has the periodicity, and (iii) to determine that the type of the mouth movement is the mouth movement by conversation if the duration is greater than the first predetermined time and if the mouth movement has no periodicity.

According to this aspect, the type of the mouth movement can be accurately determined on the basis of the duration of the mouth movement and whether or not the mouth movement has the periodicity. It is thus possible to accurately estimate the drowsiness.

(Supplementary Note 4)

In the drowsiness estimating apparatus described in Supplementary Note 4, the estimator is configured to estimate that the drowsiness of the driver is stronger, in comparison with when the duration is less than a second predetermined time, if the type of the mouth movement is determined to be the mouth movement by eating and if the duration is greater than the second predetermined time.

According to this aspect, it can be accurately determined whether or not the mouth movement by eating is intended to remove the drowsiness. It is thus possible to accurately estimate the drowsiness.

(Supplementary Note 5)

In the drowsiness estimating apparatus described in Supplementary Note 5, the drowsiness estimating apparatus is further provided with: a provider configured to provide a plurality of types of awakening stimuli for the driver; and a controller configured to control said provider to provide a different types of awakening stimuli in accordance with the type of the mouth movement.

According to this aspect, an appropriate awakening stimulus corresponding to the drowsiness can be provided. It is thus possible to remove the drowsiness of the driver.

The present disclosure may be embodied in other specific forms without departing from the spirit or essential characteristics thereof. The present embodiments and examples are therefore to be considered in all respects as illustrative and not restrictive, the scope of the disclosure being indicated by the appended claims rather than by the foregoing description and all changes which come in the meaning and range of equivalency of the claims are therefore intended to be embraced therein.

What is claimed is:

1. A drowsiness estimating apparatus comprising:
a camera configured to take an image of a face of a driver of a vehicle; and
a processor programmed to:
    detect a duration of a mouth movement of the driver and whether or not the mouth movement has periodicity, on the basis of the face image;
    determine a type of the mouth movement on the basis of the duration and whether or not the mouth movement has the periodicity, including:
        determining that the type of the mouth movement is drowsiness if the duration is less than a first predetermined time;
        determining that the type of the mouth movement is eating if the duration is greater than the first predetermined time and if the mouth movement has the periodicity; and
        determining that the type of the mouth movement is conversation if the duration is greater than the first predetermined time and if the mouth movement has no periodicity; and
    estimate drowsiness of the driver on the basis of the type of the mouth movement.

2. The drowsiness estimating apparatus according to claim 1, wherein the processor is programmed to determine whether the type of the mouth movement is one of a mouth movement by drowsiness, a mouth movement by eating, and a mouth movement by conversation.

3. The drowsiness estimating apparatus according to claim 2, wherein the processor is programmed to:
    estimate that the drowsiness of the driver is greater if the type of the mouth movement is determined to be eating and if the duration is greater than the second predetermined time; and
    estimate that the drowsiness is less if the type of the mouth movement is determined to be eating and if the duration is less than the second predetermined time.

4. The drowsiness estimating apparatus according to claim 1, wherein the processor is further programmed to:
    provide a plurality of types of awakening stimuli for the driver; and the drowsiness estimating apparatus further comprises a controller configured to control the processor to provide different types of awakening stimuli in accordance with the type of the mouth movement.

* * * * *